United States Patent [19]

Andersen et al.

[11] Patent Number: 4,702,262

[45] Date of Patent: Oct. 27, 1987

[54] ELECTROMAGNETIC APPLICATOR FOR LOCALIZING HYPERTHERMIA HEATING IN A SYSTEM

[75] Inventors: Jorgen B. Andersen; Povl Raskmark, both of Aalborg, Denmark

[73] Assignee: The Danish Hyperthermia Foundation, Aalborg, Denmark

[21] Appl. No.: 748,815

[22] Filed: Jun. 26, 1985

[30] Foreign Application Priority Data

Jun. 27, 1984 [DK] Denmark ............................ 3128/84

[51] Int. Cl.⁴ ................................................ A61N 1/40
[52] U.S. Cl. ............................... 128/804; 219/10.55 R
[58] Field of Search ............... 128/798, 802, 804, 783; 219/10.55 R, 10.57, 10.81

[56] References Cited

U.S. PATENT DOCUMENTS 3,472,233 10/1969 Senbachen ...................... 128/783 X
4,462,412 7/1984 Turner ................................ 128/804

FOREIGN PATENT DOCUMENTS 1388870 10/1971 Australia ............................. 128/798

OTHER PUBLICATIONS

Morita and Andersen, "Near-Field Absorption in a Circular Cylinder from Electric and Magnetic Line Sources", *Bioelectromagnetics*, 3:253-274, (1982).
Andersen, et al., "A Hyperthermia System Using a New Type of Inductive Applicator", *IEEE Transactions on Biomedical Engineering*, vol. BME-31, No. 1, Jan. 1984.
Raskmark and Andersen, "Focused Electromagnetic Heating of Muscle Tissue", *IEEE Transactions on Microwave Theory and Techniques*, vol. MTT-32, No. 8, Aug. 1984.

*Primary Examiner*—Lee S. Cohen
*Attorney, Agent, or Firm*—Richards, Harris, Medlock & Andrews

[57] ABSTRACT

An electromagnetic applicator (10) is provided for heating internal biological tissue, such as cancerous tumors, where applicators generate an electromagnetic field propagating across a gap (20) for forming a relative maximum power density adjacent the internal tumor volume. Conductive elements (12, 14) are spaced a predetermined distance to form a gap (20) and power is applied at radio frequencies through a balancing and matching circuit to generate the electromagnetic field which propagates across the gap (20). A plurality of applicators (10) may be placed about a body location to enable the maximum relative power density to be placed at a selected location within the body portion. A radiating dipole antenna (46) may be used to radiate a signal from which transmitted signal parameters are derived for forming a local power density maximum at a location approximated by the radiating dipole antenna (46). A controller (42) provides power source (40) outputs to applicators (10) having the same relative amplitudes and opposite phase angles of signals received from the transmitting dipole antenna (46) at locations approximating the locations of applicators (10) at the desired body location.

29 Claims, 7 Drawing Figures

ELECTROMAGNETIC APPLICATOR FOR LOCALIZING HYPERTHERMIA HEATING IN A SYSTEM

FIELD OF THE INVENTION

The present invention relates to hyperthermia systems for heating internal biological tissue and, more particularly, to a compact applicator, or a plurality of such applicators, applied to the surface of the human body for radiating electromagnetic energy to provide a controllable heating profile for treating tumors.

BACKGROUND OF INVENTION

During recent years, a number of biological and clinical results have shown that treatment of cancer may be improved when heat is applied to the cancerous tissue, especially when the heat treatment is combined with traditional cancer therapies such as radiation. Statistics on more than 800 cases show that the frequency of complete response rises from 25% when radiation alone is used to 64% when radiation is combined with a hyperthermia treatment.

Clinical results, however, are limited by the ability of hyperthermia systems to selectively heat tumors without damaging surrounding healthy tissues. Thus, noninvasive surface applicators used in conventional hyperthermia systems often obtain only superficial heating (3-5 cm in depth from the surface) because the electromagnetic wave penetration is limited by surrounding muscle tissue due to attenuation in the microwave range or due to damage from heating by strong near-field effects at low radio frequencies.

Existing applicators used for hyperthermia, i.e., heating of cancerous tumors, primarily heat superficial tumors and seldom provide for a controllable heating profile. It would be desirable to provide for the heat treatment of tumors at depths within the patient, and also provide for the treatment of tumors at non-symmetrical locations. Since the applicator is applied adjacent a patient, a suitable applicator should be compact and should have an open structure giving easy access to the patient. Many existing applicators are unsuitable for such topical application.

Where large body volumes are to be heated one known applicator system comprises a coil about the body which is excited with a radio frequency current. Such a system has a fixed power density distribution in a body which closely approximates a parabola having zero power at the center of the body. It is apparent that the surface excitation must be substantial to provide adequate heating excitation at a deep location.

Yet another large volume or whole body applicator is described in U.S. Pat. No. 4,462,412 where substantially uniform heating is produced within a cylindrical biological tissue specimen. A plurality of radiating apertures are matched with the size of the body specimen. The body specimen is actually placed within the annulus of the applicator for substantially circumferential radiation. This radiating system provides an annular phased array, where a number of applicators are provided in a fixed annular arrangement and are excited from a common source in a coherent fashion. The applicator is tuned to provide a broadband match to body absorption to minimize reflection from the body tissue back to the excitation source. This whole body application distributes power in the body tissue for deep heating, but the distribution is generally uniform and is not localized at the tumor region. Sustantial heating currents may occur near body curvatures and adjacent the feet and heat regions. An absorbing material may be provided to absorb excess radiation but with concomitant inconvenience to the patient and to the clinician operating the equipment.

A theoretical analysis, Morita and Andersen, "Near-Field Absorption in a Circular Cylinder from Electromagnetic Line Sources," 3 *Bioelectromagnetics*, 253-274 (1982), has suggested that circumferential line sources might enalbe a power density maximum to be internally localized. The study further suggested that the local relative power maximum might be moved within the cylinder of excitation by controlling the included angle of the distributed circumferential sources. However, only circumferential sources and the relative included angle of adjacent sources were considered for analysis.

A need has thus arisen for apparatus which can deliver electromagnetic radiation at deep locations in body tissue and at specific places where the application of heat is desired, with minimum heating at other locations; where the power density may be shifted around by electronic means; and which have a structure which provides for convenient application to the patient and use by the clinical staff.

The disadvantages of the prior art are overcome by the present invention, however, and an improved apparatus and focusing method are provided for localizing heating effects for hyperthermia treatments of tissue at deep body locations.

SUMMARY OF INVENTION

According to one embodiment of the present invention, an electromagnetic applicator is provided which is usable at a selected human body location for hyperthermia treatment of deep seated tumors. The applicator includes a pair of conductive sections for application to the body surface at a selected location. The conductive sections define edge portions which are spaced apart and placed adjacent the body location. The edge portions have a width which corresponds to a first dimension of the deep seated tumor and which further have a spacing which is effective to form an emitting aperture for radiating electromagnetic energy. The spacing dimension also defines a second dimension within the tumor where the first and the second dimensions define boundaries for a heated volume of the tumor for the hyperthermia treatment.

In a particular embodiment, a plurality of applicators are spaced above a tumor to be treated. The applicators are excited by power supplies which are individually controlled in amplitude and phase to form a plurality of electromagnetic fields which interact to form a relative maximum power density of the radiated fields at the tumor.

In another embodiment of the present invention, the conductive sections are cylindrical and may be segmented or continuous, with facing axially spaced apart edges. The edges define a gap which is effective to propagate an electromagnetic field within the body location when the cylindrical sections are excited at a selected frequency. This gap dimensionally cooperates with the selected frequency to define a relative maximum of the radiation electromagnetic field adjacent the deep seated tumor.

A method is provided for tuning an array of hyperthermia applicators according to the above embodiments. A transmitting element is placed within a lossy medium which is representative of a tumor location in a human body or within the body itself. The transmitted signal is detected and the received amplitude and phase are determined at selected locations for placing applicators on the human body. From the detected signal, relative amplitude and phase parameters are derived for producing an electromagnetic field from an applicator placed at each location. The amplitude and phase parameters enable the propagated wave to obtain a relative maximum power density adjacent the tumor location in the body.

These and other features and advantages of the present invention will becomes apparent from the following detailed description, wherein reference is made to the figures in the accompanying drawings.

DETAILED DESCRIPTION

Figure 1A:
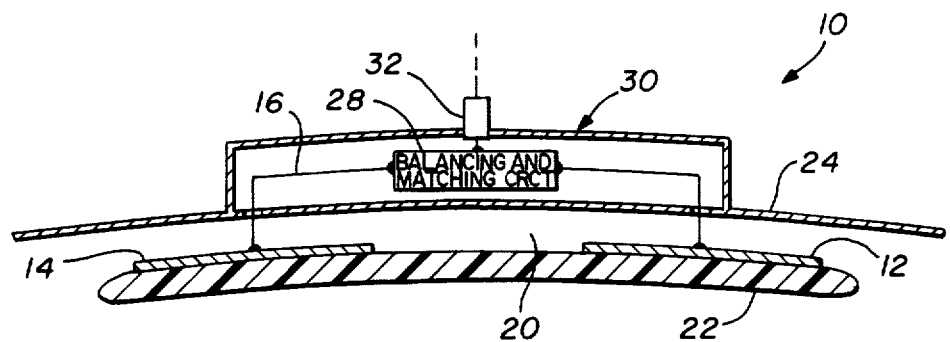
FIG. 1a is a schematic view in cross section of an applicator according to one embodiment of the present invention.

As depicted in FIG. 1a, each applicator 10 has conductive elements 12, 14 separated by a gap 20 and backed by a reflector surface 24 and with an electrically insulating layer 22 for use adjacent the surface to be irradiated. Conductive elements 12, 14 are driven in a balanced manner by a source of electromagnetic energy such that a high-frequency electromagnetic field is propagated between conductive elements 12, 14 across the gap 20.

An electromagnetic wave is radiated from gap 20 into underlying tissue and may combine with electromagnetic waves from other applicators as hereinafter discussed to form a maximum energy density within a localized volume. Applicator 10 is in direct contact with the body to be heated with conductive elements 12, 14 spaced above the body by insulating layer 22.

According to the present invention, applicators 10 may be placed in close contact with a body surface with minimum excessive surface heating tending to damage healthy tissue. Close contact between applicator 10 and underlying body tissue assures that only tissue below applicator 10 is heated rather than heating other parts of the body. Excessive surface heating by radiation from applicator 10 is minimal, and the relative power density at the center of the body to be heated has been demonstrated to be capable of being 30% higher than the power density at the surface of the body.

In one version of applicator 10, insulating layer 22 and conductive elements 12, 14 are in a planar array. In alternate embodiments, it may be advantageous to have conductive elements 12, 14 of applicator 10 that are conformable to the local body configuration. For example, elements 12 and 14 may be concave for application to generally cylindrical body parts such as legs, arms and central trunk volumes. Conforming applicator 10 to an adjacent body location may change the impedance of applicator 10 and require some external tuning to optimize impedance matching while retaining the essential features of deep heating with low surface heating. However, the localized heating available from applicator 10 enables a substantial internal volume to be heated using a relatively small number of close contact applicators on the body surface. Thus, convenient access to the patient is provided at all times during the hyperthermia treatment.

Undesirable hot spots may be created in the underlying tissue if there were direct contact between a metallic edge of conductive plates 12, 14 and the underlying tissue. Insulating layer 22 separates the tissue and the metallic edges of conductive elements 12, 14 such that large edge-effect electric fields are substantially accommodated in the essentially lossless insulating medium which forms layer 22. Numerical simulations and experiments have shown that an insulating distance of 2 to 5 mm is sufficient to eliminate these hot spots. The spacing material may be either a solid dielectric or a fluid which, at the same time, is effective to control the surface temperature.

Figure 1B:
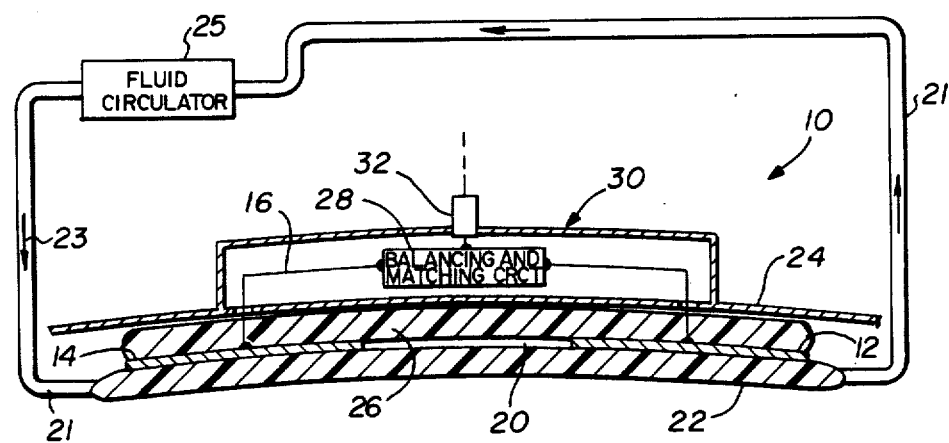
FIG. 1b is a schematic view and cross-section of an applicator according to an alternate embodiment of the present invention.

As illustrated in FIG. 1b, a network of tubing 21 may be used to circulate a fluid 23 through insulating layer 22 by means of a fluid circulator 25 to control the temperature of the fluid for cooling the surface of the treatment area over extended periods of heating.

Reflector 24 is preferably metallic to reflect radiation from gap 20 back toward the underlying tissue. Loss of radiation from gap 20 would result in a loss of heating power and could provide a hazard to other regions of the patient and to clinical personnel. Reflector 24 is sized slightly larger than conductive elements 12, 14 and the elevation of reflector 24 above conductive elements 12, 14 is not critical since it would typically remain less than the wave length at the frequencies of interest. In one embodiment, illustrated in FIG. 1b fluid used in insulator 22 also fills envelope 26 between conductive elements 12, 14 and reflector 24 for improved shielding effects which enable the reflector elevation to be further reduced as a result of the high permittivity of the fluid.

Conductive elements 12, 14 are connected through excitation leads 16 penetrating reflector 24 in a manner effective to balance conductive elements 12, 14 with respect to the reflector. Thus, if the reflector has a potential of 0 volts (i.e., grounded), conductive element 12 will have $(V/2)$ volts and conductive element 14 will have $(-V/2)$ volts. Balancing and matching circuit 28 is contained in enclosure 30 and connects through coaxial connector 32 with an external unbalanced voltage supply.

In one important aspect of the present invention the dimensions of applicator 10 are selected based on the volume and depth of the appropriate tumor to be heated as hereinafter discussed, for shielding tissue within which heating is not desired, and for providing a compact applicator 10. Thus, the impedance of applicator 10 will not necessarily be optimized with respect to the selected frequency of excitation. Circuit 28 contains well-known circuitry means for matching applicator 10 to a standard impedance level for balancing with an external power supply. Suitable balancing and matching circuits 28 are well-known; see, for example, H. L. Krauss et al., *Solid State Radio Engineering*, New York: Wiley, 1980.

Figure 2:
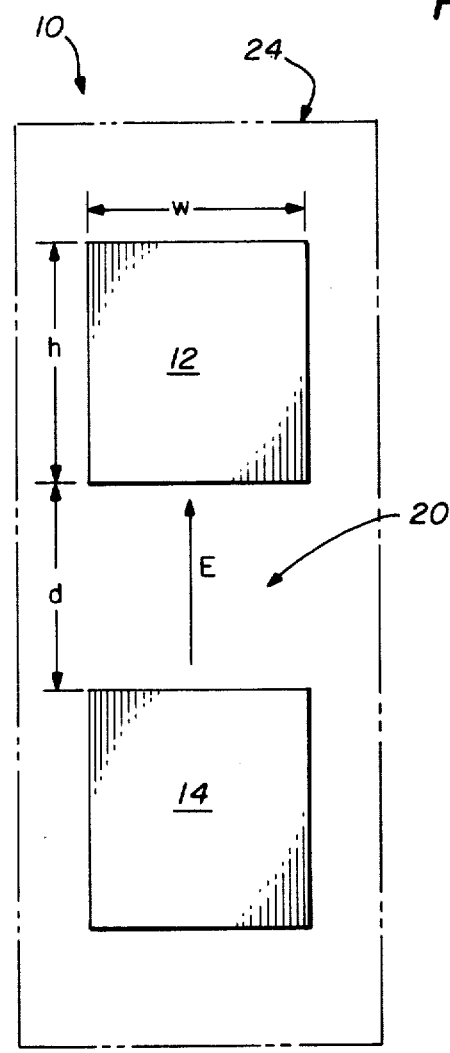
FIG. 2 is a bottom view of the applicator depicted in FIG. 1.

Referring to FIG. 2, there is shown a bottom view of applciator 10. Conductive elements 12, 14 are rectangular plates having width "w", a height "h", and separated by a distance "d" forming the gap 20. Radiating elements 12, 14 may be driven by a high-frequency voltage (not shown) in a balanced way. As well-known to those knowledgable in the field, there are equivalent ways of describing the radiation exciting source. In one description, the electrical currents running along elements 12, 14 radiate into the excitation medium. Alternatively, magnetic currents existing in gap 20 may be considered to be the exciting source. For theoretical computations, the magnetic current concept is believed to be the most useful.

As hereinafter explained, the "d" and "w" dimensions are related to the internal volume within which the local relative power density maximum is obtained. The axial extent of the primary heated volume is approximately equal to the gap 20 distance "d". Similarly, dimension "w" may be chosen to correspond to the lateral extent of the tumor if it is of a superficial type. When applicator 10 forms one element of a multi-element array, however, with "w" is preferably selected to be less than one quarter of the circumference of the body, or part of the body, in question. The height "h" is chosen such that elements 12, 14 act as a shield to prevent tissue at other locations from being heated. The height "h" is not a critical dimension, but it is typically of the order of the radius of the body or body part being treated.

Figure 3A:
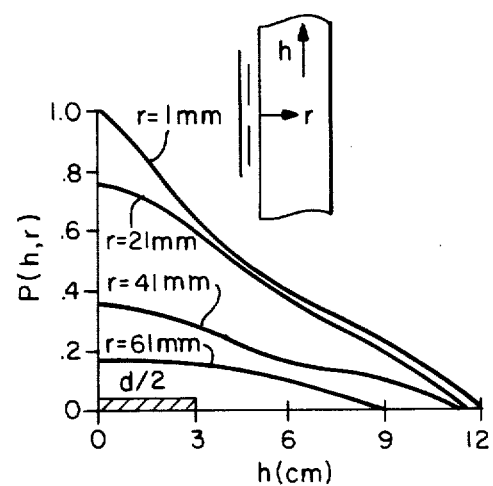
FIGS. 3a and 3b are graphical preesntations of relative power distribution in a cylinder from the applicator shown in FIGS. 1 and 2.
Figure 3B:
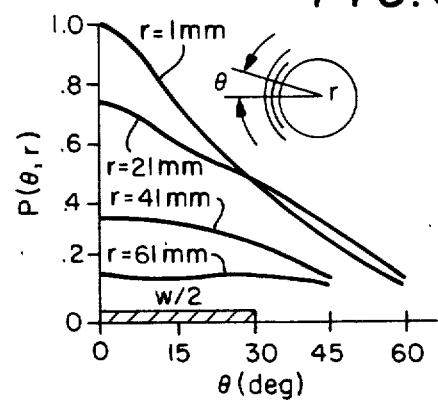

FIG. 3, graphs (a) and (b), illustrates the localized heating available at deep-seated tumor lcoations from the applicator 10 described in FIGS. 1 and 2. The applicator parameters are "d"=6 cm; "w"=12 cm (formed on a cylinder diameter of 20 cm and over an included angle of about 70°); "h"=6 cm, with an excitation frequency of 144 MHz. Insulating layer 22 is a layer of water 5 mm in thickness. Relative power densities P are plotted as a function of depth "r" beneath the surface of a cylindrical volume having a response equivalent to muscle tissue. Dimension "w" wraps over an included angle of about ±30°.

The power density distribution at deeper depths, i.e., 41 and 61 mm, is shown to be relatively uniform within an area defined by the gap spacing "d" (to ±3 cm) and the gap width "w" (to about 25°). Further, there is little or no power distribution beyond the application plate sections (h>10 cm; θ>45°). Thus, a single applicator with a radiating aperture at relatively low radio frequencies obtains the desired localized power density localized peak for heating a selected volume.

Figure 4:
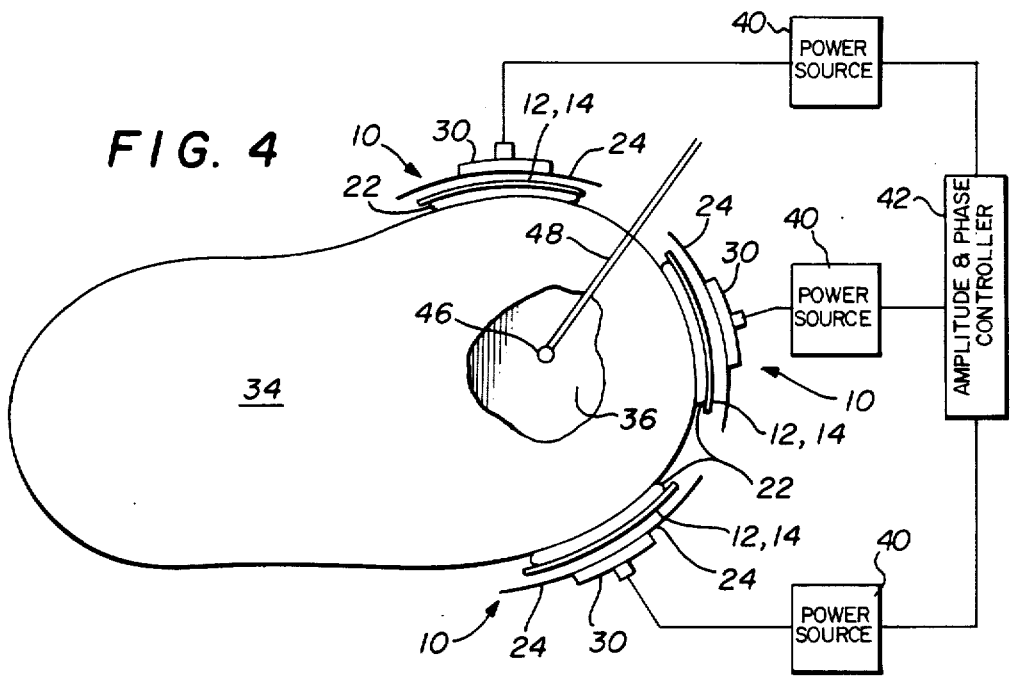
FIG. 4 is a schematic pictorial illustration of an arrangement of applciators to heat a selected tissue group at a deep body location.

In some instances, only one applicator 10 with an insulating layer 22 may be sufficient to heat the tumor to the desired treatment temperature. In other applications, the volume and depth of the tumor will be such that it is not possible to heat it sufficiently with one applicator. As shown in FIG. 4, several applicators 10 may be spaced above tumor 36 and excited in a phased relationship and with sufficient amplitude to localize the energy density adjacent tumor 36 where the localized maximum energy density may occur.

FIG. 4 depicts in schematic pictorial illustration an application of three close-contact applicator 10 for heating a cancerous tumor volume 36. Each applicator 10 includes enclosure 30 and adjoining reflector 24. Beneath reflector 24 are conductive elements 12 and 14 with gap 20 (see FIG. 2) oriented to place the propagation direction for electric field E (FIG. 2) perpencidular to the plane of the drawing. Insulating layer 22 is placed adjacent the surface of a body 34 containing tumor 36 for protecting and cooling the surface. Each applicator 10 is excited by an independent power source 40 with the application of power source 40 to each applicator 10 controlled in amplitude and phase by controller 42. Controller 42 may be selected from a number of available devices which are not within the scope of the present invention. In some instances, it will be sufficient to have excitations of equal phase and magnitude, perhaps direct from power sources 40, where three applicators 10 are spaced equidistant from the desired point of maximum heating. As indicated in FIG. 2, field E is polarized across gap "d" as represented by the arrow. The applicators are preferably co-polarized (i.e., propagating fields E in same direction) in order to obtain maximum gain, and resulting maximum heating, from applicators 10.

In one aspect of the present invention, a method is provided for maximizing the power density at a localized point, using reciprocal methods. By reciprocal methods is meant providing an invasive probe within the tumor site to emit a low power radiation at a selected polarity which is received by applicators 10 to determine the characteristics of the signal to be radiated for hyperthermia treatment. Thus, the signal finally applied by controller 42 to applicators 10 should provide an electromagnetic wave with the same relative amplitude as the received signal, but having a phase equal to the negative of the received signal. This procedure produces the desired result irrespective of tissue inhomogeneity and the excitation will be correct even in the presence of bones and other field-perturbing elements.

As more particularly shown in FIG. 4, selection of the control parameters, i.e., amplitude and phase, may be accomplished using a small, copolarized radiating element, an invasive dipole antenna 46 which is excited through cable 48. Dipole antenna 46 radiates a low-power signal which is received by applicators 10, and the relative amplitudes and phases are determined from the received signal. If the mutual coupling between the applicators is negligible due to losses in intervening tissue, and is therefore neglected, the relative amplitudes and phases for heating may be supplied by maintaining the relative amplitudes transmitted from power sources 40 identical with the received relative amplitudes and by reversing the detected phases for the transmitted signal. This process is called phase conjugation. Where mutual coupling cannot be neglected, the uncoupled result may be processed by matrix multiplication using the process described by Andersen, "Electromagnetic Heating," *Proceedings of the 4th International Symposium on Hyperthermic Oncology*, Vol. 2, pp. 113–128, Taylor & Francis, 1985.

It will be appreciated that placing dipole antenna 46 within the patient may not be possible and is certainly undesirable. A phantom model with a medium having a response similar to human body tissue may be created using techniques well-known in the art to duplicate the body section to be treated. Outputs for controller 42 are determined by placing dipole antenna 46 within the phantom model.

Figure 5:
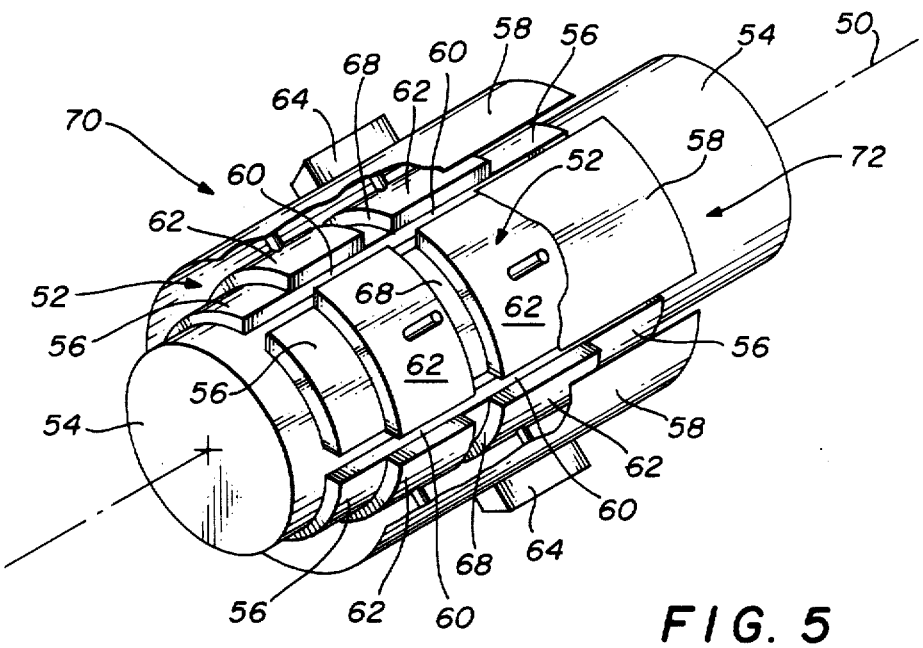
FIG. 5 is an isometric pictorial illustration of an axially spaced, cylindrically sectioned arrangement of applicators according to one embodiment of the present invention.

Referring now to FIG. 5, there is shown in isometric pictorial illustration yet another embodiment showing a sectional balanced coaxial applicator 70 having the desired properties of compactness, openness, and electronic control. The resulting applicator is especially suited to heating deep-seated tumors.

The embodiment of applicator 70 shown in FIG. 5 is designed for heating a cylindrical excitation medium 54 having electrical properties corresponding to muscle tissue. The applicator 70 is basically a lossy coaxial conductor having cylindrical medium 54 as the inner conductor and conducting cylinders 52 as the outer conductor. The outer conductor 52 is split into two cylinders formed by sectional conductive elements 62 separated by a gap 68. Across gap 68, a high frequency electrical voltage may be applied to excite an electromagnetic wave propagating into medium 54 and axially along axis 50.

As further shown in FIG. 5, the two cylinders 52 formed by sectional conductive elements 62 may be shortened to provide only two tapes or cuffs surrounding medium 54. The width of the tapes is chosen to attenuate axial wave propagation. Between excitation medium 54 and the conducting tapes 52 is placed a thin layer of electrically insulating material 56. Insulating layer 56 may be continuous or may be sectioned in correspondence with pairs of sectional conductive elements 62. The electrically insulating layer 56 acts to attenuate strong near-fields from the edges of the sectional conductive elements 62.

Shielding sections 58 each overlay a corresponding sectional conductive element 62 and separating insulator 56. Shielding sections 58 prevent excess radiation from leaking outwardly to the surrounding and further contribute to the electrical balance in the applicator assembly 70. The applicator assembly 70 may be divided into a plurality of pairs of sectional radiation elements 62 as shown in FIG. 5. Each pair of sectional radiating elements 62 is externally excited by an electrical voltage which is transformed by matching and balancing circuits conventionally housed within housing 64.

Thus, a pair of facing conductive elements 62 with their overlying shielding section 58 and underlying insulating layer 56, with external electronics in housing 64, form an independent applicator section assembly 72. A plurality of section assemblies 72 may be spaced apart by circumferential spacings 60 to obtain the openness which provides operating access to the patient by clinical personnel during the hyperthermia treatment.

Theoretical considerations have indicated that an applicator assembly 70, as hereinabove described with four pairs of conductive elements 62, may provide a power density at the center of excitation medium 54 which may be 30% greater than the power density adjacent the surface of medium 54, provided the four output signals have the same amplitude and phase. The theoretical results are presented and compared with experimental results, Raskmark and Andersen, "Focused Electromagnetic Heating of Muscle Tissue," *IEEE Transaction on Microwave Theory and Techniques*, Vol. MTT-32, No. 8 (August 1984), which disclosure is incorporated herein by reference. The analysis suggests that electric field penetration depths are related to wave length such that low frequency fields, in the 100 MHz range, might be used for increased penetration rather than "focused" fields. A frequency is chosen which is low enough to avoid exponential decay effects, yet high enough to enable constructive interference between the waves to create a local maximum.

The analysis further indicates that the width of gap 68 affects the deep power maximum. If gap 68 is too small, near-field effects can disrupt constructive interference of the propagated waves. Numerical simulations suggest that gap 68 should be larger than about one quarter of the wave length in lossy medium 54.

For example, an applicator assembly 70 has been formed with a diameter of 10 cm and excited at a frequency of 150 MHz across a gap width of 6 cm and with an insulating layer thickness of 2 mm. Subsequent experiments have verified the theoretical prediction that an internal power density may be obtained which is 30% higher than at the surface. As noted with respect to FIGS. 1–4, four coherent signals with different complex weights (i.e., amplitude and phase) may lead to an unsymmetrical power distribution, which has also been demonstrated. Thus, relative power maximums may be localized adjacent the tumor which is to be treated.

As hereinabove discussed, an applicator using four sectional applicators 72 has been described, but a different number of sections could have been used. Likewise, it is possible to unite circumferential conductive elements 62, split shields 58 and underlying layer 56 to form circumferential bands or cuffs which can be readily applied about cylindrical body sections to form a circumferential radiating gap 68.

It is therefore apparent that the present invention is one well adapted to obtain all of the aspects hereinabove set forth together with other aspects which will become obvious and inherent from a description of the apparatus and tuning method. It will be understood that certain combinations and subcombinations are of utility and may be obtained without reference to other features and subcombinations. This is contemplated by and is within the scope of the present invention.

We claim:

1. An electromagnetic applicator for applying electromagnetic energy from a source to a selected human body location for hyperthermia treatment of deep-seated tumors, comprising:

a first conductive element having a predetermined length and width dimension;

a second conductive element having a predetermined length and width dimension, said width of said second element being equal to the width of said first element;

a reflector spaced above said conductive elements for reflecting electromagnetic energy toward the selected human body location;

said first and second conductive elements having a surface adapted to be positioned adjacent the selected human body location and having a layer of lossless insulating material disposed on said surface of said conductive elements; and said first and second conductive elements being spaced apart a predetermined distance and being disposed adjacent each other to define an aperture therebetween and said aperture being the same in width as said conductive elements, the width of said conductive elements being determined by the lateral extent of the tumor and the distance between said conductive elements being determined by the distance the tumor is located beneath the surface of the body such that electromagnetic energy applied to said first and second conductive elements at a frequency to penetrate to the tumor causes electromagnetic radiation to be propagated from said aperture and defines the boundaries of the volume of heat received by the selected human body location which includes the tumor.

2. The applicator of claim 1 wherein said conductive elements have a predetermined contour to conform to a selected body location.

3. The applicator of claim 1 wherein said layer of insulating material includes a circulating fluid effective to assist in cooling surface portions of the selected human body location.

4. The applicator of claim 1 wherein the said lossless insulating material is of a thickness sufficient to accommodate the large edge-effect electric fields near the edges of said conductive elements.

5. The applicator of claim 4 wherein said lossless insulating material is of a thickness between 2 to 5 millimeters.

6. The applicator of claim 1 and further including a fluid having a high permittivity disposed between said reflector and said conductive elements whereby the reflection spacing between said conductive elements and said reflector is reduced.

7. The applicator of claim 1 and further including:
a balancing and matching circuit connected to the conductive elements and adapted for connection to the source of electromagnetic energy, such that said first and second conductive elements are balanced with respect to said reflector and the applicator is impedance matched with the source of electromagnetic energy applied to the applicator.

8. An electromagnetic applicator for applying electromagnetic energy from a source to a selected human body location for hyperthermia treatment of deep-seated tumors, comprising:
a first conductive element having a predetermined length and width dimension;
a second conductive element having a predetermined length and width dimension, said width of said second element being equal to the width of said first element;
a reflector spaced above said conductive elements for reflecting electromagnetic energy toward the selected human body location;
a balancing and matching circuit connected to the conductive elements and adapted for connection to the source of electromagnetic energy, such that said first and second conductive elements are balanced with respect to said reflector and the applicator's impedance is matchable with the electromagnetic energy source; and
said first and second conductive elements being spaced apart a predetermined distance and being disposed adjacent each other to define an aperture therebetween and said aperture being the same in width as said conductive elements, the width of said conductive elements being determined by the lateral extent of the tumor and the distance between said conductive elements forming said aperture being determined by the distance the tumor is located beneath the surface of the body, whereby electromagnetic energy applied to said first and second conductive elements of a frequency to cause electromagnetic energy to be propagated from said aperture to penetrate to the tumor to cause a volume of tissue at a selected human body location, which includes the tumor, to be heated and the boundaries of the heated volume of tissue being defined by the applicator.

9. The applicator of claim 8 wherein said conductive elements have a surface adapted to be positioned adjacent the selected human body location and further including:
a layer of lossless insulating material disposed on said surface of said conductive elements, said insulating material being of a thickness sufficient to accommodate the large edge-effect electric fields near the edges of said conductive elements forming said aperture.

10. The applicator of claim 9 and further including:
a material having a high permittivity disposed between said reflector and said conductive elements.

11. The applicator of claim 8 wherein said first and second conductive elements have a predetermined contour selected to conform to the surface of human body locations.

12. A hyperthermia system for applying electromagnetic energy to a selected human body treatment area for hyperthermia treatment of deep-seated tumors located within the treatment area of a patient, comprising:
a plurality of electromagnetic applicators, each of said applicators being independently positionable about the human body treatment area;
each of said electromagnetic applicators further including:
a first conductive element having a predetermined length and width dimension;
a second conductive lement having a predetermined length and width dimension; and
said first and second conductive elements being spaced apart a predetermined distance and being disposed adjacent each other to define an aperture therebetween and having the same width as said conductive elements, the width of said conductive elements being determined by the lateral extent of the tumor and the distance of said aperture between conductive elements being determined by the distance the tumor is located beneath the surface of the body; and
means for supplying electromagnetic energy to said plurality of applicators, whereby electromagnetic energy is applied to said applicators at a frequency to cause electromagnetic energy to be radiated from said aperture of each of said applicators into the tumor region in the selected human body treatment area with a heating pattern controlled by the independent positioning of applicators, aperture distance, and the aperture width and said independently positionable applicators permitting access to the patient.

13. The hyperthermia system of claim 12 wherein said means for supplying electromagnetic energy is an independent source of electromagnetic energy having a common frequency for each of said plurality of applicators.

14. The hyperthermia system of claim 13 wherein each of said plurality of independent power sources includes means for controlling the amplitude and phase of electromagnetic energy radiated from said plurality of applicators.

15. The hyperthermia system of claim 12 and further including:
means for controlling the amplitude and phase angle of electromagnetic energy radiated from each of said applicators, whereby a relative maximum power density is formed within the selected human body treatment location including the deep-seated tumor.

16. The hyperthermia system of claim 15 wherein said means for controlling the amplitude and phase of each of said plurality of electromagnetic applicator controls the electromagnetic wave propagated from each of said applicators to be of equal phase angle and amplitude.

17. The hyperthermia system of claim 12 wherein each of said plurality of applicators further includes:
  insulating material for selectively controlling the temperature of the surface of portions of the human body treatment area associated with each of said plurality of applicators.

18. The hyperthermia system of claim 12 wherein each of said plurality of applicators further includes:
  a reflector spaced above said conductive elements for selectively reflecting eletromagnetic energy toward portions of the human body treatment area.

19. The hyperthermia system of claim 18 and further including:
  a balancing and matching circuit connected to said means for supplying electromagnetic energy to said applicators and said conductive elements of said applicators, whereby said first and second conductive elements of each of said applicators are balanced with respect to said reflector for said applicator and the impedance of each of said applicators is matchable with the impedance of said means for supplying electromagnetic energy.

20. The hyperthermia system of claim 12 wherein each of said conductive elements of each of said applicators has a predetermined shape to conform to the surface of the human body locations.

21. A hyperthermia system for applying electromagnetic energy to a selected human body treatment area for hyperthermia treatment of deep-seated tumors located within the treatment area, comprising:
  a plurality of electromagnetic applicators, each of said applicators being independently positionable about the human body treatment area;
  means for applying a source of electromagnetic energy having a predetermined frequency;
  each of said electromagnetic applicators further including:
    a first conductive element having a predetermined length and width dimension;
    a second conductive element having a predetermined length and width dimension;
    a reflector spaced above said conductive elements for reflecting electromagnetic energy toward the selected human body location;
    means for balancing said first and second elements with respect to said reflector;
    means for matching the impedance of each of said applicators to said source of electromagnetic energy; and
  said first and second conductive elements being spaced apart a predetermined distance and being disposed adjacent each other to define an aperture therebetween and, said aperture being of the same width as said conductive elements, said width across said aperture being determined by the lateral extent of the tumor and said distance between said aperture being determined by the distance the treated tumor is located beneath the surface of the human body; and
  said conductive elements having a surface adapted to be positioned adjacent the human body treatment area and further having a layer of lossless insulating material disposed on said surface of said conductive elements, said insulating material is of a sufficient thickness to accommodate the large edge-effect electric fields near the edges of said conductive elements, whereby electromagnetic energy is applied to said applicators at a frequency to cause electromagnetic energy to be radiated from said aperture of each of said applicators to penetrate into the tumor region in the human body to generate a volume of heated tissue controllable by the independent positioning of each of said applicators in direct contact with the surface of the human body and further by the selection of the predetermined width across the aperture and the distance between said conductive elements forming said aperture of each of said applicators and the frequency of said source of electromagnetic energy to thereby heat deep-seated tumors.

22. The hyperthermia system of claim 21 and further including:
  a dielectric mateiral disposed between said conductive elements and said reflector of said applicators and said material having a high permittivity such that the spacing between said reflector and said conductive elements is reduced.

23. The hyperthermia system of claim 21 wherein said lossless insulating material is attached to each of said applicators, whereby each applicator and its insulating material are independently positionable as a unit in direct contact with the surface of the human body.

24. The hyperthermia system of claim 23 wherein said insulating material associated with each of said applicators is a circulating fluid effective in independently cooling the region of the human body beneath each of said applicators.

25. The hyperthermia system of claim 21 wherein said insulating material is a circulating fluid effective in cooling the surface of the human body in the region beneath said applicators.

26. The hyperthermia system of claim 21 and further including:
  means for independently controlling the amplitude and phase of the electromagnetic energy propagated by each of said applicators, whereby a relative maximum power density is formed within the human body location including the deep-seated tumor.

27. The hyperthermia system of claim 21, wherein said means for applying a source of electromagnetic energy is an independent power source for each of said applicators, wherein said power sources have a common frequency.

28. The hyperthermia system of claim 21, wherein said means for balancing and means for matching is a balancing and matching circuit within each of said applicators.

29. The hyperthermia system of claim 21, wherein said width of said applicator is less than one-quarter of the circumference of the human body part subject to the treatment.

* * * * *

UNITED STATES PATENT AND TRADEMARK OFFICE
CERTIFICATE OF CORRECTION

PATENT NO.  : 4,702,262
DATED       : October 27, 1987
INVENTOR(S) : Jorgen B. Andersen; Povl Raskmark It is certified that error appears in the above-identified patent and that said Letters Patent is hereby corrected as shown below:

Column 2, line 1, "Sustantial" should be -- Substantial --.

Column 2, line 11, "enalbe" should be -- enable --.

Column 2, line 65, "radiation" should be -- radiated --.

Column 3, line 27, "preesntations" should be -- presentations --

Column 5, line 6, "applciator" should be -- applicator --.

Column 5, line 67, "applicator" should be -- applicators --.

Column 7, line 37, "radiation" should be -- radiating --.

Column 10, line 31, "lement" should be -- element --.

Column 12, line 26, "mateiral" should be -- material --.

Signed and Sealed this

Fifth Day of July, 1988

Attest:

DONALD J. QUIGG

Attesting Officer

Commissioner of Patents and Trademarks